United States Patent
Scheuzger

(10) Patent No.: US 6,660,865 B2
(45) Date of Patent: Dec. 9, 2003

(54) PROCESS FOR THE PREPARATION OF QUINOLINE DERIVATIVES

(75) Inventor: Karl Scheuzger, Schweizerhalle (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 10/312,122

(22) PCT Filed: Jun. 26, 2001

(86) PCT No.: PCT/EP01/07258

§ 371 (c)(1), (2), (4) Date: Dec. 20, 2002

(87) PCT Pub. No.: WO02/00625

PCT Pub. Date: Jan. 3, 2002

(65) Prior Publication Data

US 2003/0181724 A1 Sep. 25, 2003

(30) Foreign Application Priority Data

Jun. 28, 2000 (CH) .............................. 1274/00

(51) Int. Cl.[7] ...................... C07D 215/24; C07D 215/28
(52) U.S. Cl. ...................... 546/174; 546/180; 546/178; 546/152
(58) Field of Search ................. 546/174, 180, 546/178, 152

(56) References Cited

U.S. PATENT DOCUMENTS 5,380,852 A * 1/1995 Schutze et al. ............. 546/174

FOREIGN PATENT DOCUMENTS

EP 0094349 11/1983

OTHER PUBLICATIONS

"Synthesis of New Antibacterial and Antifungal Derivatives of 8–hydroxyquinoline", Margaret Ungureanu et al., An. Stint. Univ., "AL. I. CUZA" IASI, Chim. pp. 55–60 (1999).
"Synthesis of Aroxylacetic Acids Di–Catalyzing Method", Yuzhou Wang et al., 1993.
"Synthesis of Some Quinoline Derivatives", Van Tong Nguyen, et al., 1995.

* cited by examiner

Primary Examiner—Charanjit S. Aulakh
(74) Attorney, Agent, or Firm—Rose M. Allen

(57) ABSTRACT

Compounds of formula (I), wherein $R_1$ is hydrogen or chlorine and $R_2$ is hydrogen, $C_1$–$C_8$alkyl, or $C_1$–$C_8$ alkyl substituted by $C_1$–$C_6$alkoxy or by $C_3$–$C_6$alkenyloxy, can be prepared by: a) introducing the major portion of the amount to be reacted of a compound of formula (II) into a solvent mixture comprising at least one organic solvent capable of forming an azeotrope with water, and at least one aprotic-dipolar solvent; b) metering in an aqueous strong base in an amount equivalent to that major portion of the total amount of the compound of formula (II); c) adding the remaining portion of the amount to be reacted of the compound of formula (II); d) adding a weak base in an amount that is at least equivalent to that remaining portion; e) removing the water from the reaction mixture by azeotropic distillation; f) adding a compound of formula (III), wherein $R_2$ is as defined for formula (I); and g) isolating the resulting compound of formula (I) from the reaction mixture.

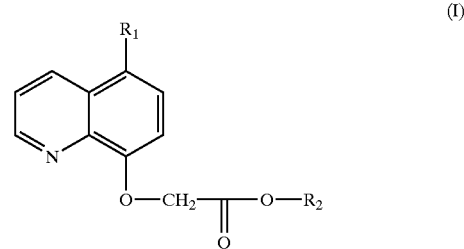

(I)

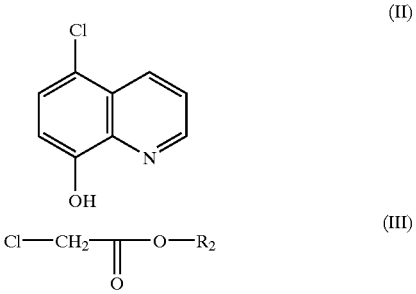

(II)

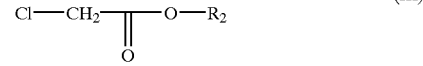

(III)

2 Claims, No Drawings

PROCESS FOR THE PREPARATION OF QUINOLINE DERIVATIVES

This application is a 371 of PCT/EP/01/07258 filed Jun. 26, 2001, now WO 02/00625.

The present invention relates to a process for the preparation of quinoline derivatives by reacting 8-hydroxyquinolines with chloroacetic acid esters.

Quinoline derivatives used for protecting cultivated plants from the phytotoxic action of herbicides are known, for example, from EP-A-0 094 349 and US-A-5 441 922.

According to EP-A-0 094 349, such quinoline derivatives can be prepared by reacting 8-hydroxyquinolines with chloroacetic acid derivatives in the presence of a base in an inert solvent at elevated temperature. The yields obtained are not satisfactory, especially for the large-scale preparation of those compounds. Furthermore, undesirable by-products, e.g. alcohols, which significantly reduce product quality, are formed in that process.

The aim of the present invention is accordingly to provide a process for the preparation of quinoline derivatives that is distinguished by high yields and good product quality and that avoids the disadvantages of the known processes.

The process according to the invention for the preparation of compounds of formula I

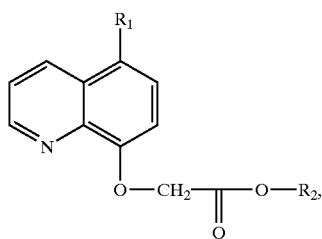

(I)

wherein $R_1$ is hydrogen or chlorine and $R_2$ is hydrogen, $C_1$–$C_8$alkyl, or $C_{1-C8}$alkyl substituted by $C_1$–$C_6$alkoxy or by $C_3$–$C_6$alkenyloxy, comprises a) introducing the major portion of the amount to be reacted of a compound of formula II

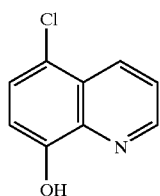

(II)

into a solvent mixture comprising at least one organic solvent capable of forming an azeotrope with water, and at least one aprotic-dipolar solvent;
b) metering in an aqueous strong base in an amount equivalent to that major portion of the total amount of the compound of formula II;
c) adding the remaining portion of the amount to be reacted of the compound of formula II;
d) adding a weak base in an amount that is at least equivalent to that remaining portion;
e) removing the water from the reaction mixture by azeotropic distillation;
f) adding a compound of formula III

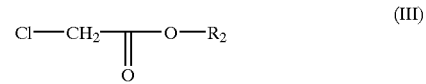

(III)

wherein $R_2$ is as defined for formula I; and
g) isolating the resulting compound of formula I from the reaction mixture.

The compound of formula I can be isolated, for example, by precipitating from water and filtering, followed by drying. Special preference is given to isolation of the compound of formula I from the reaction mixture by, after completion of reaction step f), distilling off the solvents, preferably under reduced pressure, especially in vacuo. After distilling off the solvents, a small amount of acetic acid is preferably added to the product melt in order to neutralise the excess of base, and water is then added in order to remove the salts. The aqueous phase is separated off and the organic product phase is again extracted with water. The extractions with water are carried out preferably at temperatures of from 80° C. up to the boiling temperature of the reaction mixture, especially at a temperature of from 90 to 95° C.

After the second aqueous phase has been separated off, the water still dissolved in the product melt can be distilled off under reduced pressure, especially in vacuo.

The starting compound of formula II is used in the process according to the invention in two portions. The major portion, preferably from 0.70 to 0.98 molar equivalent (of a total of 1 molar equivalent), especially 0.95 molar equivalent, is used as initial charge at the start of the process and the remaining portion is added after addition of the strong base. Before being added, the remaining portion is preferably made into a slurry in a solvent having aprotic-dipolar properties, especially N-methylpyrrolidone. It is advantageous to use the same solvent as that already used for the major portion of the total amount of the compound of formula II.

The weak base is added either in an amount equivalent to that remaining portion or in an excess, preferably in an amount of from 1 to 3 molar equivalents, especially 2 molar equivalents, based on the remaining portion of the compound of formula II.

Organic solvents capable of forming an azeotrope with water are, for example, toluene or xylene or mixtures thereof, preferably toluene.

Solvents having aprotic-dipolar properties are, for example, N-methylpyrrolidone, dimethyl-formamide, dimethylacetamide and acetonitrile or mixtures thereof, preferably N-methyl-pyrrolidone.

Within the context of the present invention, strong bases are preferably the hydroxides of alkali metals and alkaline earth metals, especially sodium hydroxide and potassium hydroxide.

Within the context of the present invention, weak bases are preferably the carbonates of alkali metals and alkaline earth metals, especially sodium carbonate and potassium carbonate.

The compound of formula III is metered in an equivalent amount or in a slight excess relative to the total amount of compound of formula II used. Preference is given to the use of a slight excess, especially from 1.01 to 1.1 equivalents, more especially from 1.01 to 1.03 equivalents, very especially 1.02 equivalents, of compound of formula III. The reaction of the compound of formula II with the compound of formula III is preferably carried out under reduced pressure, especially at a pressure of from 10 to 50 kPa, more especially at 25 kPa.

The strong base is added at room temperature or, preferably, at elevated temperature, especially at a temperature of from 40 to 50° C., more especially from 42 to 45° C.

The compound of formula II is reacted with the compound of formula III at elevated temperature, preferably at from 75 to 85° C., especially from 78 to 80° C.

The process according to the invention has a number of advantages over the prior art: In the dry state, the compound of formula II used as starting material can be handled only with utmost difficulty as extremely large amounts of dust are formed. For that reason the compound is, as a rule, stored in a form that contains water of crystallisation and it is usually also available commercially in that form (water content generally from about 30 to 50%). The water content of the compound of formula II used is generally highly variable so that, after the azeotropic distillation with toluene, it is necessary to determine the exact content of compound of formula II in the mixture; otherwise, the amount of the other reactants to be used cannot be calculated with sufficient accuracy and excessive or insufficient amounts may therefore be metered in, resulting in significant losses of yield and/or in a reduction in product quality. The process according to the invention avoids those disadvantages by means of the special process procedure in the following simple manner.

At the start of the process, a portion of the starting compound of formula II is used as initial charge and the strong base is metered in until the compound of formula II has been quantitatively converted to the corresponding salt. When the pH is measured continuously during addition of the base, that point in time can be simply recognised by a jump in the pH curve (pH>13, i.e. free hydroxyl ions appear after conversion to the salt is complete). On the basis of the known consumption of strong base, the amounts of the other starting materials can then be calculated exactly.

A further advantage of the process according to the invention is that the isolated product of formula I can be obtained in the form of a melt and can also be stored in that form. Isolating the compound of formula I in the form of a dry product is, in contrast, laborious and time-consuming because, in the case of preparation on a n industrial scale, the drying process for removing residual water can last up to a week.

Preparation Example

Preparation of 2-(5-chloroguinolin-8-yloxy)-1-methylhexyl ester of formula 4.01

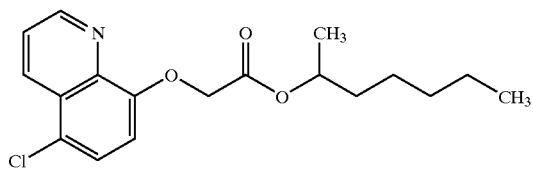

(4.01)

To a mixture of 1705 kg (about 0.95 eq.) of 5-chloro8-hydroxyquinoline (about 70% containing water of crystallisation) in 1400 kg of toluene and 3200 kg of N-methylpyrrolidone in a stirred vessel there is added, at a temperature of from 42 to 45° C., 30% aqueous sodium hydroxide in portions until the addition of a portion gives rise to a jump in pH of >0.5 and, at the same time, the pH is >13 (about 740 to 840 kg). The amount of 5-chloro-8-hydroxyquinoline calculated from the consumption of aqueous sodium hydroxide is then added in 200 kg of N-methyl pyrrolidone so that the total amount is 1 equivalent (about 63 kg). After azeotropically distilling off the water, potassium carbonate is added (about 97 kg, corresponding to 0.1 eq., based on the total amount of 5-chloro-8-hydroxyquinoline used). 1.02 equivalents of chloroacetic acid 1-methylhexyl ester are then added to the reaction mixture at a temperature of from 78 to 82° C. and a pressure of from 25 to 30 kPa. After the reaction is complete and the solvents have been distilled off in vacuo up to a temperature of 120° C., 80 kg of 80% acetic acid are then added at 80–95° C. 4500 litres of demineralised water are then added at a temperature of 80–95° C. After separation into layers, the lower product melt at a temperature of 80–95° C. is separated off into 3700 litres of demineralised water at a temperature of 80–95° C. in a second reactor. After separation into layers, the lower product melt at a temperature of 80–95° C. is separated off into a further reactor and the residual water remaining in dissolved form is distilled off from the product melt in vacuo at a temperature of from 80 to 115° C. 2310 kg (94% of theory, based on the 5-chloro8-hydroxyquinoline) of 2-(5-chloroquinolin-8-yloxy)-1-methylhexyl ester having a content of 95% are obtain ed.

The process according to the invention is especially suitable for the preparation of the compounds set out in the following Table 1:

TABLE 1

Compounds of formula I:

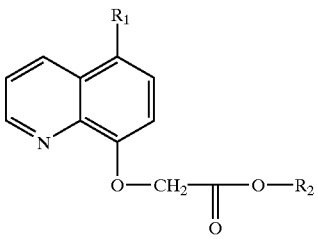

(I)

| Cmpd. No. | $R_1$ | $R_2$ |
|---|---|---|
| 4.01 | Cl | —CH(CH$_3$)-n-C$_5$H$_{11}$ |
| 4.02 | Cl | —CH(CH$_3$)—CH$_2$OCH$_2$CH═CH$_2$ |
| 4.03 | Cl | H |
| 4.04 | Cl | n-C$_4$H$_9$ |

The process according to the invention is very especially suitable for the preparation of compound no. 4.01.

What is claimed is:

1. A process for the preparation of a compound of formula I

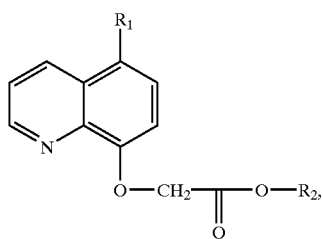

(I)

wherein
$R_1$ is hydrogen or chlorine and
$R_2$ is hydrogen, $C_1$–$C_8$alkyl, or $C_1$–$C_8$alkyl substituted by $C_1$–$C_6$alkoxy or by $C_3$–$C_6$alkenyloxy, which process comprises
 a) introducing the major portion of the amount to be reacted of a compound of formula II

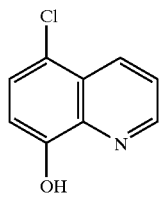

(II)

into a solvent mixture comprising at least one organic solvent capable of forming an azeotrope with water, and at least one aprotic-dipolar solvent;
 b) metering in an aqueous strong base in an amount equivalent to that major portion of the total amount of the compound of formula II;
 c) adding the remaining portion of the amount to be reacted of the compound of formula II;
 d) adding a weak base in an amount that is at least equivalent to that remaining portion;
 e) removing the water from the reaction mixture by azeotropic distillation;
 f) adding a compound of formula III

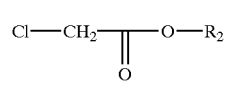

(III)

wherein $R_2$ is as defined for formula I; and
 g) isolating the resulting compound of formula I from the reaction mixture.

2. A process according to claim 1, wherein the compound of formula I is isolated from the reaction mixture by, after completion of reaction step f), distilling off the solvents from the product melt, extracting the product melt with water and then separating off the aqueous phase from the product melt.

* * * * *